(12) United States Patent
Proctor et al.

(10) Patent No.: US 7,531,683 B2
(45) Date of Patent: May 12, 2009

(54) CONTINUOUS PROCESS FOR THE CYANATION OF HYDROGENATED β-KETOESTERS

(75) Inventors: Lee David Proctor, Macshal'n (GB); Anthony John Warr, Chester (GB)

(73) Assignee: Phoenix Chemicals Limited (GB)

( * ) Notice: Subject to any disclaimer, the term of this patent is extended or adjusted under 35 U.S.C. 154(b) by 715 days.

(21) Appl. No.: 10/515,272

(22) PCT Filed: May 21, 2003

(86) PCT No.: PCT/GB03/02173

§ 371 (c)(1),
(2), (4) Date: Nov. 19, 2004

(87) PCT Pub. No.: WO03/097581

PCT Pub. Date: Nov. 27, 2003

(65) Prior Publication Data

US 2005/0154224 A1    Jul. 14, 2005

(30) Foreign Application Priority Data

May 22, 2002   (GB) ................. 0211715.8

(51) Int. Cl.
*C07C 253/30* (2006.01)
*C07C 69/66* (2006.01)
(52) U.S. Cl. ...................................... 558/346; 560/179
(58) Field of Classification Search ................. 558/346; 560/179
See application file for complete search history.

(56) References Cited

U.S. PATENT DOCUMENTS 7,057,064 B2 *   6/2006   Proctor et al. ............... 560/179

FOREIGN PATENT DOCUMENTS

| EP | 1 077 212 A1 | 2/2001 |
| JP | 2003038193 | 2/2003 |
| WO | WO 99/32434 A1 | 7/1999 |
| WO | WO 00/46186 A1 | 8/2000 |
| WO | WO 03/004459 A2 | 1/2003 |

OTHER PUBLICATIONS

PCT International Search Report; International Application No. PCT/GB 03/ 02173, Applicant: Phoenix Chemicals Limited.
Kwak, Byong-Sung, *Continuous processes for the synthesis of pharmaceutical fine chemicals*, Specialty Chemicals Magazine, article, Jun. 2002, pp. 17-18.

\* cited by examiner

*Primary Examiner*—Johann Richter
*Assistant Examiner*—Ebenezer Sackey
(74) *Attorney, Agent, or Firm*—Brooks Kushman P.C.

(57) ABSTRACT

The present invention relates to a continuous process for the cyanation of hydrogenated β-ketoesters in a cyanation zone maintained under conditions of temperature and pressure effective for cyanation of a hydrogenated R-ketoester. A substrate comprising a hydrogenated β-ketoester is continuously supplyed to the cyanation zone together with a cyanide. The substrate is contacted with the cyanide in the cyanation zone for a period effective for at least partial cyanation of the hydrogenated β-ketoester and a product stream is continuously extracted from the cyanation zone.

16 Claims, 1 Drawing Sheet

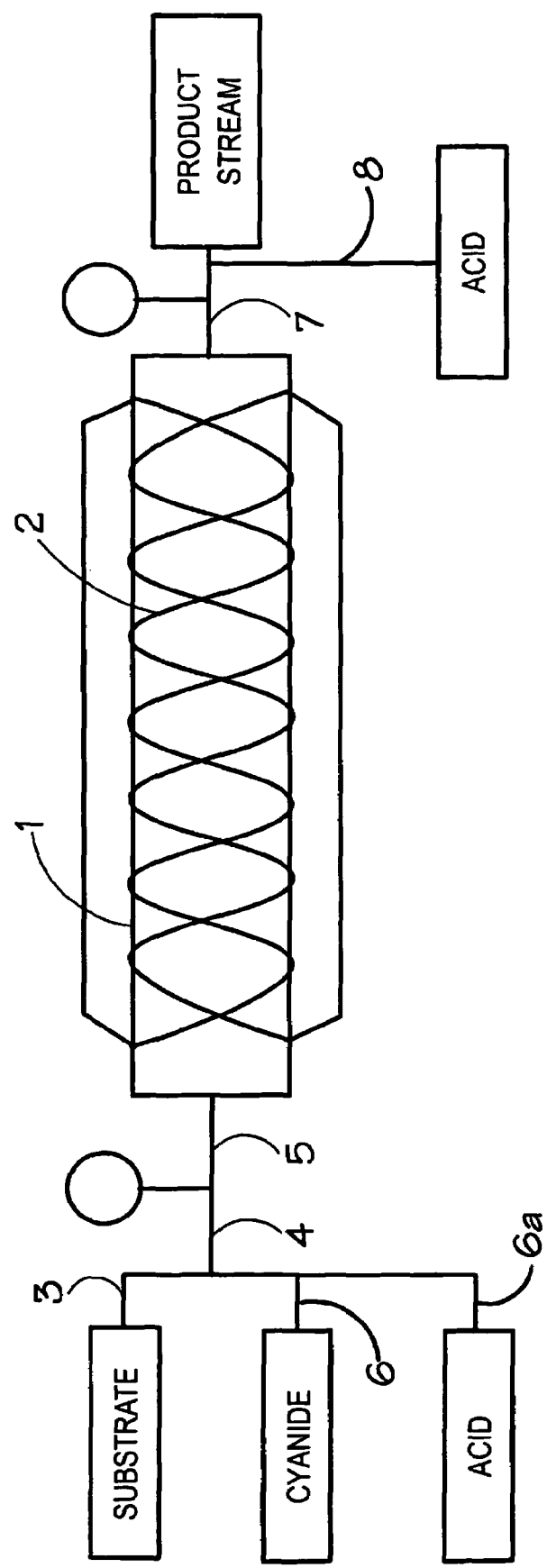

CONTINUOUS PROCESS FOR THE CYANATION OF HYDROGENATED β-KETOESTERS

BACKGROUND OF THE INVENTION

1. Field of the Invention

The present invention relates to a continuous process for the cyanation of hydrogenated β-ketoesters.

2. Background Art

Cyanated, hydrogenated β-ketoesters are useful as pharmaceutical intermediates. One particularly useful intermediate is (R)-ethyl-4-cyano-3-hydroxybutyric acid ester of the formula (1)

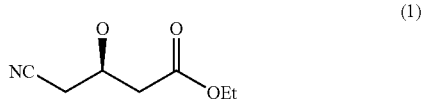

which is used in the preparation of hypolipidernic agents. There have been a number of reports of the preparation of this compound, and of compounds of this type. For example, JP-A-2001114739 discloses a method for producing lower alkyl esters of (R)-4-cyano-3-hydroxybutyric acid from lower alkyl esters of (S)-4-halogen-3-hydroxybutyric acid by means of a cyanation reaction which comprises carrying out a distillation after filtering an organic solvent phase obtained by extracting and separating the lower alkyl ester of the (R)-4-cyano-3-hydroxybutyric acid from a reaction liquid after cyanation.

JP-A-19970254804 discloses a method for purifying a crude (R)-4-cyano-3-hydroxybutyric acid lower alkyl ester, formed from the cyanation of an (S)-4-chloro-3-hydroxybutyric acid lower alkyl ester by distillation in the presence of a solvent. Japanese Patent No. 2001302607 discloses a process for the cyanation of a halogenohydroxybutyrate at from 90° C. to 120° C. in an organic solvent or mixed aqueous organic solvent.

JP-A-19990018144 discloses a method for producing a lower alkyl ester of (R)-4-cyano-3-hydroxybutyric acid comprising carrying out a cyanation reaction on an (S)-4-halogeno-3-hydroxybutyric acid and then adding an acid and regulating the pH of the reaction solution.

JP-A-2001122841 discloses a method for producing (R)4-cyano-3-hydroxybutyric acid lower allyl ester comprising cyanation of the corresponding (S)-4-halogeno-3-hydroxybutyric acid lower alkyl ester and then extracting the reaction product several times using an organic solvent.

Japanese Patent No. 2001114738 discloses a method for the cyanation of (S)-4-halogeno-3-hydroxybutyric acid lower alkyl esters and extraction of the reaction product with organic solvent.

JP-A-2001114739 discloses a process for the manufacture of (R)-4-cyano-3-hydroxybutyric acid lower alkyl esters from the cyanation of (S)-4-halo-3-hydroxybutyric acid lower alkyl esters, followed by extracting the ester formed from the reaction solution, filtering the organic solvent phase and distilling.

WO-A-00/46186 discloses a process for preparing (R)-4-cyano-3-hydroxybutyric acid ester derivatives by cyanation and sequential esterification (S)-3,4-epoxybutyric acid salt as a starting material.

Despite extensive investigation of methods for producing (R)-4-cyano-3-hydroxybutyric acid ester derivatives, there remains a need for an improved commercial process. Each of the prior art processes suffer from one or more of the following disadvantages: poor yield; low conversion rate; use of expensive and/or unnecessary reagents or solvents; purification problems; lack of stereoselectivety; suitability only for laboratory scale preparation; or other unsuitability for commercial scale operation. It is therefore an object of the present invention to provide an improved process for the cyanation of hydrogenated β-ketoesters, in particular a continuous process for such cyanation which may be operated on a commercial scale.

SUMMARY OF THE INVENTION

According to the present invention, there is provided a continuous process for the cyanation of hydrogenated β-ketoesters comprising:
(a) providing a cyanation zone;
(b) maintaining the cyanation zone under conditions of temperature and pressure effective for cyanation of a hydrogenated β-ketoester;
(c) continuously supplying to the cyanation zone a substrate comprising a hydrogenated β-ketoester;
(d) continuously supplying to the cyanation zone a cyanide;
(e) contacting the substrate with the cyanide in the cyanation zone for a period effective for at least partial cyanation of the hydrogenated β-ketoester; and
(f) continuously extracting from the cyanation zone a product stream comprising a cyanated β-ketoester.

The cyanation zone is preferably maintained at a temperature of from about 20° C. to about 200° C., more preferably from about 80° C. to about 150° C., still more preferably from about 90° C. to about 120° C.

The cyanation zone is preferably maintained at a pressure of from about 500 mbar to 200 bar.

The cyanide is preferably in the form of an alkali metal cyanide, for example sodium cyanide. The equivalency of cyanide (i.e. moles of cyanide per mole of hydrogenated β-ketoester) is preferably maintained at a molar ratio of from about 1.0 to about 4.0, more preferably from about 2.0 to about 3.0.

Preferably, in the process of the invention, the product stream continuously extracted from the cyanation zone is continually quenched before being extracted. This step may be conducted in a separate quench reactor and a suitable quenching agent is glacial acetic acid. However, other suitable quenching acids include sulphuric acid, nitric acid, hydrochloric acid and phosphoric acid.

The residence time of the reaction product mixture in the cyanation zone is preferably substantially less than 8 minutes, for example less than about 7 minutes, more preferably less than about 6 minutes and most preferably less than about 5 minutes. Residence times of from about 5 seconds to about 300 seconds, preferably from about 22 seconds to about 60 seconds, are preferred.

The hydrogenated β-ketoester preferably has the formula (2):

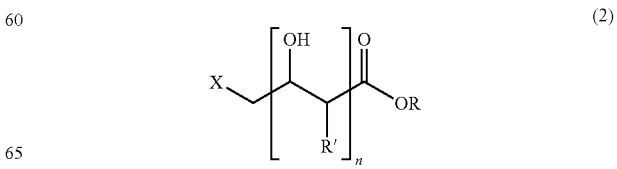

wherein X, R and R' are independently selected from hydrogen, optionally substituted alkyl, aryl, alkenyl, aralkyl or alkaryl groups or optionally substituted cycloalkyl groups;

and wherein X may alternatively be selected from fluorine, chlorine, bromine, iodine, mesylates, tosylates, sulphonate esters, tetraalkyl ammonium and other suitable leaving groups; and n is from 1 to 4.

The β-ketoester may have from 1 to 4 keto groups and may, for example, be a β, δ-diketoester.

The process of the present invention is preferably carried out in the presence of an aqueous solvent, which may be supplied to the cyanation zone in combination with the hydrogenated β-ketoester. Preferably, the solvent is water. Preferably, a small quantity of an acidic material is added to the reaction mixture. Preferably, such acid material (eg acetic acid or a mineral acid) is added in an amount effective to push the equilibrium in aqueous solution between $CN^-$ and HCN in favour of $CN^-$.

The product is conveniently purified by steam distillation.

The cyanation zone may be any suitable shape or size and may be adapted from a shell and tube heat exchanger.

The starting material for the process of the invention may be produced by any known means. However, it is preferred that the starting material also be generated by means of a continuous process. Accordingly, the present invention further provides a continuous process for the enantioselective catalytic hydrogenation and subsequent cyanation of β-ketoesters comprising:

[A] providing a catalytic hydrogenation zone maintained under conditions of temperature and pressure effective for the catalytic hydrogenation of β-ketoesters;

[B] providing a cyanation zone maintained under conditions of temperature and pressure effective for cyanation of a hydrogenated β-ketoester;

[C] continuously supplying to the catalytic hydrogenation zone a substrate comprising a β-ketoester to be hydrogenated, a catalyst effective for enantioselective hydrogenation of the β-ketoester and hydrogen;

[D] contacting the substrate, the catalyst and the hydrogen in the hydrogenation zone for a residence time effective for at least partial enantioselective catalytic hydrogenation of the β-ketoester;

[E] continuously withdrawing from the hydrogenation zone a reaction product mixture comprising enantioselectively hydrogenated β-ketoester, unreacted β-ketoester, catalyst and hydrogen;

[F] supplying the reaction product mixture to a separation zone and separating at least some of the enantioselectively hydrogenated β-ketoester from the reaction product mixture;

[G] withdrawing the separated enantioselectively hydrogenated β-ketoester as intermediate product;

[H] optionally supplying at least part of the remaining material from the separation zone to the hydrogenation zone;

[I] continuously supplying intermediate product from step [G] to the cyanation zone.

[J] continuously supplying to the cyanation zone a cyanide;

[K] contacting the hydrogenated β-ketoester with the cyanide in the cyanation zone for a period effective for at least partial cyanation of the hydrogenated β-ketoester; and

[L] continuously extracting from the cyanation zone a product stream comprising a cyanated β-ketoester.

Preferably, the hydrogenation zone is maintained at a pressure of at least about 75 bar, more preferably at least about 90 bar and still more preferably at least about 100 bar. In one preferred process according to the invention, the hydrogenation zone is maintained under conditions of from about 100 to about 150 bar.

The catalytic hydrogenation zone is preferably maintained at a temperature of at least about 75° C., more preferably at least about 90° C. and even more preferably at least about 100° C. In one preferred process according to the invention, the catalytic hydrogenation zone is maintained at a temperature of from about 100 to about 150° C.

The process of the invention may be operated without a solvent. However, in certain processes according to the invention, a solvent may be used. For example, a solvent may be selected from ethanol/dichloromethane and methanol/ethanol. A particularly preferred solvent system is acetone/methanol.

The hydrogenation catalyst is any catalyst effective for enantioselective hydrogenation of β-ketoesters but is preferably a BINAP or other bisaryl bisphosphine- based ligand catalyst, for example $[NH_2Et_2]^+[RuCl\{p\text{-MeO-BINAP}\}_2\{\mu\text{-Cl}\}_3]^-$, $[NH_2Et_2]^+RuCl(p\text{-MeO-BINAP})_2(\mu\text{-Cl})_3]$, [RuI(p-cymene)(p-MeO-BINAP)], [RuI(p-cymene)(p-Tol-BINAP)]I, [RuI(p-cymene)(m-Tol-BINAP)]I, [RuI(p-cymene)(3,5-(t-Bu)$_2$-BINAP)]I, [RuI(p-cymene)(p-Cl-BINAP)]I, [RuI(p-cymene)(p-F-BINAP)]I, [Ru(p-cymene)(3,5-(Me)$_2$-BINAP)]I, [RuI(p-cymene)(H$_8$-BINAP)]I, [RuI(p-cymene)(BIMOP)]I, [RuI(p-cymene)(FUMOP)]I, [RuI(p-cymene)(BIFUP)]I, [RuI(p-cymene)(BIPHEM)]I,[RuI(p-cymene)(MeOl-BIPHEP)]I, $[RuCl_2(\text{tetraMe-BITIANP})(DMF)_n]$, $[RUcl_2(BITIANP)(DMF)_n]$,$[RuBr_2(BIPHEMP)]$, $[RuBr_2(\text{MeO-BIPHEMP})]$, $[RuCl(BI_2NAP)](MeCN)$, $[Ru_2Cl(p\text{-TolBINAP})]_2(MeCN)$, $[RuCl_2(\text{MeO-BIPHEP})]_2(MeCN)$, $[RuCl_2(BIPHEP)]_2(MeCN)$, $[RuCl_2(BIPHEMP)]_2$, or $[Ru(\eta^3\text{-2-Me-allyl})_2(\text{MeO-BIPHEP})]$ or a combination of two or more thereof.

The process of the invention is particularly useful for manufacturing intermediate compounds which may be used to make Statin drugs such as Atorvastatin (Lipitor), Fluvastatin (Lescol) and Rosuvastatin (Crestor). Existing methods for manufacturing the asymmetric unit in such drugs are described, for example, in WO-A-98/04543, U.S. Pat. Nos. 5,292,939 and 6,114,566.

A key requirement in the manufacture of a symmetrically hydrogenated β-ketoesters is the so-called "enantiomeric excess in the product of the desired enantiomer over the non-desired enantiomer. In the process of the invention, the enantiomeric excess in the product is preferably greater than about 95%, more preferably greater than about 96%, yet more preferably greater than about 97% and most preferably greater than about 98%, for example about 99% or more.

In the process of the invention, the substrate/catalyst molar ratio in the hydrogenation zone is preferably at least about 15,000:1, more preferably at least about 20,000:1, even more preferably at least about 30,000:1 and most preferably at least about 40,000:1, for example 50,000:1 or more. Substrate/catalyst molar ratios of up to about 65,000:1, or even higher, may also be contemplated in the process of the invention.

BRIEF DESCRIPTION OF THE DRAWINGS

The process of the invention will now be more particularly described with reference to the following drawing, in which:

FIG. 1 represents a schematic diagram of a plant constructed and arranged to operate in accordance with the process of the invention.

DETAILED DESCRIPTION OF THE PREFERRED EMBODIMENT(S)

Referring to FIG. 1, there is shown a cyanation zone 1 which is heated by means of a heat exchanger 2. In this example, cyanation zone 1 is maintained at temperature from about 90° C. to about 120° C. A substrate comprising, in this example, (S)-ethyl-4-chloro-3-hydroxybutyrate in water is supplied via lines 3, 4 and 5 to cyanation zone 1. Sodium cyanide is supplied in line 6 and passes through lines 4 and 5 into cyanation zone 1. Preferably an acidic material such as acetic acid is added in line 6a. The cyanation reaction takes place inside cyanation zone 1 and a product stream comprising R-ethyl-4-cyano-3-hydroxybutyrate is extracted in line 7 after a suitable residence time. Suitable residence times in the reactor may be from about 5 seconds to about 300 seconds, more preferably from about 20 seconds to about 80 seconds. The product stream is quenched by an acid supplied in line 8.

It will be appreciated that the configuration of plant, pipework, control valves, pumps, release valves, flow controllers and other items of standard equipment shown are illustrated by way of example only and that the process of the invention is not limited to the schematic configuration of plant shown in FIG. 1.

The plant illustrated in FIG. 1 is was used in a continuous cyanation process as described in the following Examples.

EXAMPLE 1

A first feed tank was charged with a 14.7% (w/w) aqueous solution of sodium cyanide. A second feed tank was charged with (S)-ethyl-4-chloro-3-hydroxybutyrate. Both tanks were connected by tubing to a reactor which was heated to 105° C. and maintained at atmospheric pressure. The sodium cyanide solution was continuously fed into the reactor at a flow rate of 0.14 ml/minute by means of a pump. The (S)-ethyl-4-chloro-3-hydroxybutyrate was continuously fed into the reactor at a flow rate of 0.80 ml/minute by means of a pump. At these flow rates the residence time in the reactor of the combined reaction product mixture was 48 seconds. The crude product stream exiting the reactor was continuously quenched by the addition of a solution comprising 6.9% (w/w) glacial acetic acid in ethyl acetate at a flow rate of 0.94 ml/minute. Product isolation was achieved by separating the ethyl acetate phase followed by evaporation at ~30 mbar and ~60° C. The active yield of (R)-ethyl-4-cyano-3-hydroxybutyrate was 67.4%.

EXAMPLE 2

A first feed tank was charged with a 15% (w/w) aqueous solution of sodium cyanide. A second feed tank was charged with an 80% w/w aqueous solution of acetic acid. A third feed tank was charged with (S)-ethyl-4-chloro-3-hydroxybutyrate. The sodium cyanide and acetic acid solutions were mixed at a molar ratio of 21:1 using a plug flow reactor element with a 1.4-second residence time at ambient temperature. The mixture was continuously fed into a two-stage plug flow reactor element into which (S)-ethyl-4-chloro-3-hydroxybutyrate was continuously fed such that the molar ratio of cyanide to substate was 2:1. The two stage reactor element consisted of an initial pre-mixer with a 4.5 second residence time and a secondary mixer with a 72 second residence time, both mixing elements being contained within a heat transfer medium such that the reaction temperature was maintained at between 105° C. and 110° C. The mixture was then continuously quenched using additional 80% acetic acid in a plug flow reactor element with a residence time of 4.0 seconds at ambient temperature. The quench acid flow rate was adjusted to maintain the crude product flow stream at a pH of between 5.0 and 5.5. The crude product was obtained as an aqueous solution, which was subjected to steam distillation to remove contaminants. The aqueous residue was then extracted with dichloromethane and the product (R)-4-cyano-3-hydroxybutyric acid was isolated in 80% chemical yield after solvent evaporation and simple vacuum distillation.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

The invention claimed is:

1. A continuous process for the cyanation of hydrogenated β-ketoesters having the formula (2):

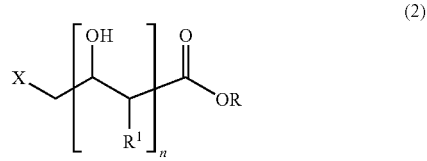

(2)

wherein X, R and $R^1$ are independently selected from hydrogen, optionally substituted alkyl, aryl, alkenyl, aralkyl or alkaryl groups or optionally substituted cycloalkyl groups and wherein X may alternatively be selected from fluorine, chlorine, bromine, iodine, mesylates, tosylates, sulphonate esters, tetralkyl ammonium and other suitable leaving groups; and n is from 1 to 4, the process comprising:
 (a) providing a cyanation zone;
 (b) maintaining the cyanation zone at a temperature of from 20° C. to 200° C. and at a pressure of from 500 mbar to 500 bar, effective for cyanation of a hydrogenated β-ketoester of formula (2);
 (c) continuously supplying to the cyanation zone a substrate comprising a hydrogenated β-ketoester of formula (2);
 (d) continuously supplying to the cyanation zone a cyanide;
 (e) contacting the substrate with the cyanide in the cyanation zone for a residence time of less than 8 minutes effective for at least partial cyanation of the hydrogenated β-ketoester; and
 (f) continuously extracting from the cyanation zone a product stream comprising a cyanated β-ketoester.

2. A process according to claim 1, wherein the cyanation zone is maintained at a temperature of from 80° C. to 150° C.

3. A process according to claim 2, wherein the cyanation zone is maintained at a temperature of from 90° C. to 120° C.

4. A process according to claim 1 wherein the cyanide is in the form of an alkali metal cyanide.

5. A process according to claim 4, wherein the cyanide is sodium cyanide.

6. A process according to claim 1, wherein the equivalency of cyanide expressed as moles of cyanide per mole of hydrogenated β-ketoester is maintained at a molar ratio of from 1.0 to 4.0.

7. A process according to claim 6, wherein the equivalency of cyanide is maintained at a molar ratio of from 2.0 to 3.0.

8. A process according to claim 1, wherein the cyanation reaction is carried out in the presence of an aqueous solvent.

9. A process according to claim 1, wherein the product stream continuously extracted in step (f) is quenched with acid.

10. A process according to claim 1, wherein the product stream is subjected to distillation to obtain a desired purified product.

11. A process according to claim 2, wherein the cyanide is in the form of an alkali metal cyanide.

12. A process according to claim 3, wherein the cyanide is in the form of an alkali metal cyanide.

13. A process according to claim 2, wherein the equivalency of cyanide expressed as moles of cyanide per mole of hydrogenated β-ketoester is maintained at a molar ratio of from 1.0 to 4.0.

14. A process according to claim 3, wherein equivalency of cyanide expressed as moles of cyanide per mole of hydrogenated β-ketoester is maintained at a molar ratio of from 1.0 to 4.0.

15. A process according to claim 4, wherein equivalency of cyanide expressed as moles of cyanide per mole of hydrogenated β-ketoester is maintained at a molar ratio of from 1.0 to 4.0.

16. A process according to claim 5, wherein equivalency of cyanide expressed as moles of cyanide per mole of hydrogenated β-ketoester is maintained at a molar ratio of from 1.0 to 4.0.

\* \* \* \* \*